United States Patent [19]

Heindl et al.

[11] Patent Number: 4,835,175
[45] Date of Patent: May 30, 1989

[54] INDOLE DERIVATIVES PHARMACEUTICAL PREPARATIONS BASED THEREON, AND β-RECEPTOR STIMULATION THEREWITH

[75] Inventors: Josef Heindl; Olaf Loge, both of Berlin, Fed. Rep. of Germany

[73] Assignee: Schering Aktiengesellschaft, Berlin and Bergkamen, Fed. Rep. of Germany

[21] Appl. No.: 917,445

[22] Filed: Oct. 10, 1986

Related U.S. Application Data

[63] Continuation of Ser. No. 617,872, Jun. 6, 1984, abandoned, which is a continuation of Ser. No. 367,868, Apr. 13, 1982, abandoned.

[30] Foreign Application Priority Data

Apr. 13, 1981 [DE] Fed. Rep. of Germany ....... 3115993

[51] Int. Cl.[4] .................... C07D 209/42; A61K 31/40
[52] U.S. Cl. ...................................... 514/419; 548/492
[58] Field of Search ......................... 548/492; 514/419

[56] References Cited

U.S. PATENT DOCUMENTS 3,696,120 10/1972 Troxler ............................... 548/492
3,705,907 12/1972 Troxler ............................... 548/492
4,229,464 10/1980 Kampe et al. ........................ 548/492

OTHER PUBLICATIONS

"β2-Agonists containing metabolically ... ", Eur. J. Med. Chem.-Chem. Ther., 1985-20, No. 1, pp. 51-55, Albrecht, R. et al.
Troxler et al, Helv. Chem. Acta, vol. 51 (1968) pp. 1616-1625, English Translation.

Primary Examiner—David B. Springer
Attorney, Agent, or Firm—Millen & White

[57] ABSTRACT

Indole derivatives of Formula I

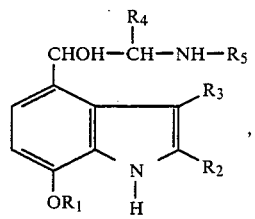

wherein
$R_1$ is hydrogen, alkyl of 1–6 carbon atoms, or benzyl
$R_2$ is hydrogen, alkyl of up to 4 carbon atoms, free or esterified hydroxyalkyl of up to 4 carbon atoms, or free, amidated or esterified carboxy or carboxyalkyl,
$R_3$ is hydrogen or alkyl containing 1–6 carbon atoms,
$R_4$ is hydrogen or alkyl containing 1–6 carbon atoms and
$R_5$ is hydrogen, or alkyl, alkenyl, or cycloalkyl, all of which per se contain up to 6 carbon atoms, and all of which are optionally substituted by a free or esterified carboxy group or by an optionally substituted phenyl group; or a polymethylene group of up to 8 carbon atoms linking the first indole residue to a second indole residue of Formula Ia

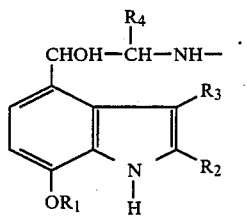

wherein
$R_1$, $R_2$, $R_3$, and $R_4$ are as defined above,
and the physiologically acceptable salts thereof with acids and, optionally, their alkali metal and alkaline earth metal salts, possess valuable pharmacological properties, such as stimulating β-receptors and prevention of premature labor, are described.

31 Claims, No Drawings

INDOLE DERIVATIVES PHARMACEUTICAL PREPARATIONS BASED THEREON, AND β-RECEPTOR STIMULATION THEREWITH

This is a continuation of application Ser. No. 617,872, filed June 6, 1984, abandoned, which is a continuation application of Ser. No. 367,868, filed Apr. 13, 1982, abandoned.

The present invention relates to novel indole derivatives, a process for their production and pharmaceutical preparations containing them.

SUMMARY OF THE INVENTION

It is an object of this invention to provide new pharmacologically active compounds which have advantageous properties.

Upon further study of the specification and appended claims, further objects and advantages of this invention will become apparent to those skilled in the art.

These objects have been attained by providing new indole derivatives of Formula (I)

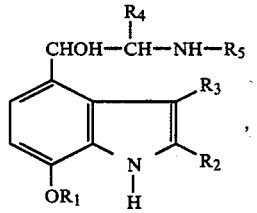

wherein $R_1$ is hydrogen, alkyl of 1-6 carbon atoms, or benzyl $R_2$ is hydrogen, alkyl of up to 4 carbon atoms, free or esterified hydroxyalkyl of up to 4 carbon atoms, or free, amidated or esterified carboxy or carboxyalkyl, $R_3$ is hydrogen or alkyl containing 1-6 carbon atoms, $R_4$ is hydrogen or alkyl containing 1-6 carbon atoms and $R_5$ is hydrogen, or alkyl, alkenyl, or cycloalkyl, all of which per se contain up to 6 carbon atoms, and all of which are optionally substituted by a free or esterified carboxy group or by an optionally substituted phenyl group; or a polymethylene group of up to 8 carbon atoms linking the first indole residue to a second indole residue of Formula Ia

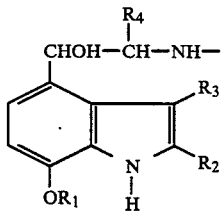

wherein $R_1$, $R_2$, $R_3$, and $R_4$ are as defined above, and the physiologically acceptable salts thereof with acids and, optionally, their alkali metal and alkaline earth metal salts.

DETAILED DISCUSSION

Examples of the alkyl groups in $R_1$, $R_2$, $R_3$, $R_4$, and $R_5$ of the novel indole derivatives include: methyl, ethyl, sec-butyl, isobutyl, tert-butyl, n-pentyl, isoamyl, n-hexyl, etc.

Examples of hydroxyalkyl groups $R_2$ include hydroxymethyl, 2-hydroxyethyl, 2-hydroxypropyl, 3-hydroxypropyl, etc. Esters of these hydroxyalkyl groups include, for example, those derived from $C_{1-6}$-alkanoic acids, e.g., acetates, propionates, butyrates, isobutyrates, valerates, caproates, etc.

Examples of $R_2$ and $R_5$ alkyl groups substituted by a carboxy group include: 2-carboxyethyl, 2- or 3-carboxy-n-propyl, 2-carboxyisopropyl; 2-, 3-, or 4-carboxy-n-butyl, 1-, 3-, or 4-carboxy-sec-butyl, etc. The alkyl portion of such groups can contain 1–6 C atoms for $R_5$ and 1–4 C atoms for $R_2$.

Esters of these groups and of the carboxy groups include those wherein the esterifying moiety (i.e., the group bonded to COO—) is $C_{1-8}$-alkyl, phenyl, $C_{1-4}$-alkoxy-$C_{1-4}$-alkyl, cycloalkylalkyl, $C_{1-4}$-alkanoyloxy-$C_{1-4}$-alkyl, di-$C_{1-4}$-alkyl-amino-$C_{1-4}$-alkyl or is of the formula

wherein X is $C_{4-6}$-alkylene wherein one C-atom is optionally replaced by one O or N atom, for example, the methyl ester, the ethyl ester, the n-propyl ester, the isopropyl ester, the n-butyl ester, the sec-butyl ester, the tert-butyl ester, the pentyl ester, the isopentyl ester, the hexyl ester, the heptyl ester, the octyl ester, the methoxymethyl ester, the ethoxymethyl ester, the propoxymethyl ester, the isopropoxymethyl ester, the butoxymethyl ester, the isobutoxymethyl ester, the tert-butoxymethyl ester, the acetoxymethyl ester, the propionyloxymethyl esters, the butyryloxymethyl esters, the isobutyryloxymethyl esters, the 2-dimethylaminomethyl esters, the 2-methylethylaminomethyl ester, the 2-diethylaminoethyl ester, the 2-pyrrolidinoethyl ester, the piperidinoethyl ester, and the morpholinoethyl ester.

Suitable amides of these groups and of the carboxy groups included the amides themselves, the $C_{1-4}$-alkylamides, e.g., the methylamides, ethylamides, propylamides, isopropylamides, etc. and the amides formed from aminoacetylmethyl ester or other aminoacetyl ester groups, e g., —NHCH$_2$COO—$C_{1-4}$-alkyl groups.

In all of the foregoing definitions of suitable esterifying and amidating groups, the alkyl portions can optionally be interrupted by one O or N atom or a -COO- group substituted by a carboxy group.

Suitable $C_{2-6}$ alkenyl groups $R_5$ include, for example, those corresponding to the above mentioned $C_2$-$C_6$-alkyl groups, e.g., propenyl, 2-butenyl, 3-butenyl, 2-isobutenyl, etc.

Examples of suitable $C_{3-6}$ cycloalkyl or (cycloalkyl)alkyl residues for $R_2$ and $R_5$ include cyclopentyl, cyclopentylmethyl, cyclohexyl, cyclopropyl, cyclobutyl, etc.

The optional, free or esterified carboxy substituents for the $R_5$ groups include those defined above for $R_2$. Suitable substituents for the substituted (preferably monosubstituted) phenyl substituent for $R_5$ groups include OH, $C_{1-4}$-alkoxy, $C_{1-4}$-alkyl or halogen (F, Cl, or Br). Generally there are 1–2 substituents, preferably one.

The polymethylene group linking the two indole residues preferably contains 1–8 C-atoms and can be branched. For such dimeric compounds, it is preferred, but not necessary, that the two indole residues be identical.

Suitable salts include those derived from physiologically acceptable acids such as hydrochloric acid, phosphoric acid, sulfuric acid, oxalic acid, succinic acid, tartaric acid etc.

The present invention concerns the racemic indole derivatives of this invention as well as their optical antipodes.

Indole derivatives are conventionally contained as active agents in commercial preparations, such as, for example, pindolol, i.e., 1-(4-indolyloxy)-3-(isopropylamino)-2-propanol, or mepindolol, i.e , 1-[4-(2methylindolyl)oxy]-3-isopropylamino-2-propanol. These active agents, showing a certain structural analogy to the indole derivatives of this invention, as is known, are $\beta$-receptor blockers (beta blockers).

In contrast, the indole derivatives of this invention, especially the esters, surprisingly, are $\beta$-receptor stimulants. Moreover, they exhibit antiallergic, antiinflammatory, and analgesic activities. The free acids of Formula I and their alkali metal salts or alkaline earth metal salts are, in most cases, less effective; they are also suitable, inter alia, as intermediates for the synthesis of highly efficacious esters. In general, all compounds of this invention are useful to prepare other compounds of this invention. Due to their $\beta$-receptor-stimulating activity, the indole derivatives of this invention evoke dilation of the bronchi and accordingly are suitable for treating diseases of the respiratory tract such as, for example, bronchial asthma, and act as labor-suppressing (labor-terminating) agents (effect tocolysis), so that they can be employed for the prevention of premature labor.

The compounds can be administered, e.g., to mammals, including humans, orally, by injection, infusion, or inhalation in accordance with conventional considerations. Typically, dosages are 5–500 mg/kg/day when administered, e.g., orally. Their administration is fully conventional unless otherwise indicated herein and can be conducted, e.g., by analogy to the administration of chromogly cique acid.

To prepare inhalants, the indole derivatives can be conventionally pulverized, or they can be dissolved or suspended in a suitable solvent and combined with suitable additives, such as diluents, suspension aids, propellant gases, flavor-ameliorating agents, etc. Typically, concentrations are 0.1–5.0 wt. %. Other unit dosages are usually 26–50 mg.

In accordance with conventional procedures, the thus-produced inhalants can furthermore be enhanced by other active agents, such as, for example, antibiotics.

For oral administration, suitable are, for example, tablets, dragees, and capsules containing, in addition to the active ingredient, a pharmacologically inert carrier, such as, for example, lactose, amylose, talc, gelatin, magnesium stearate, and similar materials, along with the customary additives.

The indole derivatives of this invention can be prepared by fully conventional procedures, e.g., by (a) reducing an indole derivative of Formula II, optionally, while simultaneously splitting off the benzyl groups

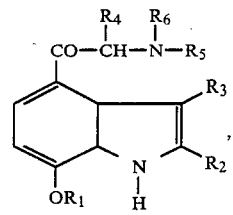

wherein
$R_1$, $R_2$, $R_3$, $R_4$, and $R_5$ are as defined above and
$R_6$ is hydrogen or benzyl, or (b) cleaving by hydrogenation an indole derivative of Formula I wherein
$R_1$ is benzyl,
and, optionally, saponifying any present ester groups or esterifying free acids, or converting the thus-obtained compounds into salts thereof.

The former reaction can be conducted, for example, by hydrogenating the compounds of Formula II in an inert solvent in the presence of palladium or platinum catalysts, e.g., at temperatures of 0°–50° C. See, e.g., Arthur I. Vogel: A Textbook of Practical Organic Chemistry, Lonqmanns, Green and Co. London etc. Third Edn. 1956, pages 870 to 874, 877 to 886, which is incorporated by reference herein.

On the other hand, however, it is also possible to conventionally reduce the compounds, for example, with complex metal hydrides incapable of reducing carboxy groups or alkoxycarbonyl groups, e.g., sodium borohydride. If an optical antipode of the racemate is to be preferably produced, it may be advantageous to conduct one of the conventional asymmetric reductions described in Houben-Weyl, "Methoden der organischen Chemie" [Methods of Organic Chemistry] 4th edition, vol. IV/2: 535 et seq. (1955), whose disclosure is incorporated by reference herein.

The mostly unknown starting compounds of Formula II can be fully conventionally prepared in various ways, for example, from indole derivatives of Formula III

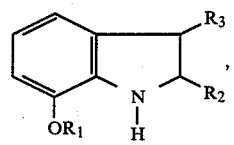

wherein $R_1$, $R_2$, and $R_3$ are as defined above. The latter compounds are well-known or can be readily prepared from known compounds using fully conventional methods.

These compounds can be condensed, for example, under the usual conditions of the Hoesch synthesis with a nitrile of Formula IV

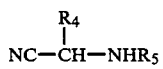

wherein $R_4$ and $R_5$ are as defined above, for example, by reacting the compounds of Formula III and the nitrile in the presence of Lewis acids in an inert solvent with introduction of hydrogen chloride gas. See, e.g. Arthur I. Vogel: A Textbook oF Practical Organic Chemistry Longmanns, Green and Co., Third Edn. 1956, pages 727 ff, whose disclosure is incorporated by reference herein. The compounds of Formula IV are also either known or readily preparable from known compounds using fully conventional methods e.g., by condensing of an α-halogene nitril with an amine.

On the other hand, the indole derivatives of Formula III can be reacted under fully conventional conditions of the Friedel-Crafts acylation (e.g., in an inert solvent in the presence of aluminum chloride) with an α-haloalkanoyl halogenide of Formula V

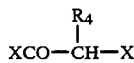
(V)

wherein

X is preferably a chlorine atom, but also can be a bromine atom, and $R_4$ is as defined above, and the thus-prepared compounds of Formula VI

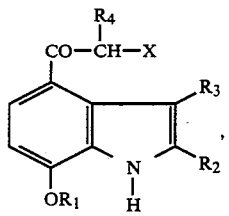
(VI)

wherein $R_1$, $R_2$, $R_3$, $R_4$, and X have their corresponding meanings as defined above, can be conventionally condensed with an amine of Formula VII

 (VI)

wherein $R_5$ is as defined above e.g., Arthur I. Vogel: A Textbook of Practical Organic Chemistry; Longmanns, Green and Co., Third Edn., 1956, pages 508 ff. The compounds of formulae V–VII are also well-known or readily preparable from known compounds using fully conventional methods.

The following examples exlain the process of this invention and describe methods for preparation of the compounds of Formula II which are starting compounds for the process of this invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A. A solution of 56.7 g of 7-methoxyindole-2-carboxylic acid in 300 ml of methanol is combined with 250 ml of methanol saturated with hydrogen chloride and heated under reflux for 2 hours. The solution is then cooled intenvisely in an ice-methanol bath, the separated crystals are vacuum-filtered and washed with a small amount of cold methanol. Yield: 26.5 g of the methyl ester of 7-methoxy-indole-2-carboxylic acid, mp 118°–119° C.

B. A solution of 42.7 g of 7-methoxyindole-2-carboxylic acid methyl ester in 950 ml of dichloromethane is cooled to −65° C. under nitrogen and with agitation. Then 65 ml of boron tribromide is added dropwise to the solution at this temperature, the mixture is stirred for 15 minutes at this temperature, and the reaction mixture is allowed to warm up to room temperature and agitated for one more hour. The mixture is thereafter stirred into 800 ml of ice water, the organic phase is separated, the aqueous phase is extracted once more with ethyl acetate, and the combined organic phases are dried with sodium sulfate. Then the mixture is evaporated to dryness under vacuum, the residue is recrystallized from acetonitrile, and the yield is 31.0 g of 7-hydroxyindole-2-carboxylic acid methyl ester, mp 218°–220° C.

C. A solution of 5.6 g of aluminum chloride in 20 ml of nitrobenzene, cooled to 10° C., is combined with 1.9 g of 7-hydroxyindole-2-carboxylic acid methyl ester and 925 mg of aminoacetonitrile hydrochloride and then the mixture is cooled to 5°–10° C. At this temperature, gaseous hydrogen chloride is conducted for 8 hours into the reaction mixture; the latter is allowed to stand overnight and then poured into ice water. After 10 minutes, the thus-produced precipitate is vacuum-filtered, the crude product is recrystallized from 2N hydrochloric acid/methanol ½, and the yield is 1.8 g of 4-aminoacetyl-7-hydroxyindole-2-carboxylic acid methyl ester hydrochloride, mp above 280° C.

D. A solution of 1.14 g of 4-aminoacetyl-7-hydroxyindole-2-carboxylic acid methyl ester hydrochloride in 200 ml of methanol is combined with 110 mg of 10% palladium catalyst on active carbon and hydrogenated for 3 hours under shaking at normal pressure. The reaction mixture is then filtered and the filtrate evaporated to dryness. The residue is vigorously stirred with acetone/methanol 9/1; the resultant product is filtered off and dried under vacuum, thus obtaining 1.0 g of 4-(2-amino-1-hydroxyethyl)-7-hydroxyindole-2-carboxylic acid methyl ester hydrochloride, decomposition point 280° C.

EXAMPLE 2

A. At 0° C., 1.7 g of methylaminoacetonitrile hydrochloride and 3.0 g of 7-hydroxyindole-2-carboxylic acid methyl ester are added to a solution of 8.4 g of aluminum chloride in 30 ml of nitrobenzene. Then gaseous hydrogen chloride is introduced into the thus-obtained solution at −4° to −2° C. for 6 hours, whereafter the reaction mixture is stirred for 16 hours at the same temperature, poured into ice water, agitated for another 10 minutes, and the precipitate is vacuum-filtered and discarded. The filtrate is combined with petroleum ether, the precipitate is vacuum-filtered, extracted by boiling with ethanol, and vacuum-filtered to remove it from the undissolved matter. Yield: 1.1 g of 4-methylaminoacetyl-7-hydroxyindole-2-carboxylic acid methyl ester hydrochloride, decomposition point 255°–256° C.

B. A solution of 896 mg of 4-methylaminoacetyl-7-hydroxyindole-2-carboxylic acid methyl ester hydrochloride in 30 ml of methanol is combined with 150 mg of 10% palladium-animal charcoal catalyst and hydrogenated under shaking at normal pressure. The reaction mixture is then filtered and the filtrate evaporated to dryness under vacuum. The residue is extracted by boiling with 20 ml of acetonitrile and the insoluble proportion is vacuum-filtered and recrystallized from ethanol, thus producing 232 mg of 4-(1-hydroxy-2-methylaminoethyl)- 7-hydroxyindole-2-carboxylic acid methyl ester hydrochloride, decomposition point 177°–180° C.

EXAMPLE 3

A. A solution of 11.2 g of aluminum chloride in 40 ml of nitrobenzene is combined with 2.8 g of isopropylaminoacetonitrile hydrochloride and 4.0 g of 7-hydroxyindole-2-carboxylic acid methyl ester. Then gaseous hydrogen chloride is introduced into the mixture at 0° C. for 4½ hours; the mixture is stirred for 16 hours at 0° C. and then poured into ice water. The precipitate is vacuum-filtered, washed with water and petroleum ether, and dried. The resultant product is suspended in a small amount of acetone, vacuum-filtered, washed with diethyl ether, and extracted by boiling with 50 ml of ethanol. The undissolved substance is vacuum-filtered, washed with cold ethanol, and dried, thus obtaining 1.18 g of 7-hydroxy-4-isopropylaminoacetylindole-2-carboxylic acid methyl ester hydrochloride, decomposition point 273° C.

B. A solution of 1.6 g of 7-hydroxy-4-isopropylaminoacetylindole-2-carboxylic acid methyl ester hydrochloride in 80 ml of methanol is combined with 300 mg of 10% palladium-animal charcoal and shaken for 2¼ hours under normal pressure with hydrogen. The reaction mixture is then filtered and the filtrate evaporated to dryness under vacuum. The residue is triturated with acetonitrile, cooled to 0° C., and filtered, thus obtaining 1.41 g of 4-(1-hydroxy-2-isopropylaminoethyl)-7-hydroxyindole-2-carboxylic acid methyl ester, decomposition point 137°–139° C.

EXAMPLE 4

658 mg of 4-(1-hydroxy-2-isopropylaminoethyl)-7-hydroxyindole-2-carboxylic acid methyl ester hydrochloride is dissolved in 20 ml of 1N sodium hydroxide solution and stirred for 45 minutes at room temperature. The reaction mixture is then cooled in an ice bath, acidified with concentrated acetic acid, agitated for another 10 minutes, and the crystallized product is vacuum-filtered and washed with water and ethanol. Yield: 383 mg of 4-(1-hydroxy-2-isopropylaminoethyl)-7-hydroxyindole-2-carboxylic acid, decomposition point above 173° C.

EXAMPLE 5

Under the conditions of Example 3(A), 10.0 g of 7-hydroxyindole-2-carboxylic acid methyl ester and 7.8 g of tert-butylaminoacetonitrile hydrochloride are reacted with each other and worked up, thus obtaining 4.8 g of 4-tert-butylaminoacetyl-7-hydroxyindole-2-carboxylic acid methyl ester hydrochloride, decomposition point 271° C.

3.4 g of the product obtained is hydrogenated under the conditions of Example 3(B) and worked up, thus producing 3.0 g of 4-(2-tert-butylamino-1-hydroxyethyl)-7-hydroxyindole-2-carboxylic acid methyl ester hydrochloride, decomposition point 168°–173° C.

EXAMPLE 6

Under the conditions of Example 4, 500 mg of 4-(tert-butylamino-1-hydroxyethyl)-7-hydroxyindole-2carboxylic acid methyl ester hydrochloride is hydrolyzed and worked up, thus obtaining 435 mg of 4-(2-tert-butyl-amino-1-hydroxyethyl)-7-hydroxyindole-2-carboxylic acid, decomposition point 260°–261° C.

EXAMPLE 7

A. 181 g of oxalic acid diethyl ester is added dropwise to a suspension of 31.3 g of potassium ethylate in 700 ml of diethyl ether. Then 51.7 g of 3-methyl-2-nitroanisole is added in incremental portions to the reaction mixture and the latter is heated for 18 hours under reflux. The mixture is allowed to cool, the resultant precipitate is vacuum-filtered, washed with diethyl ether, and dissolved in a mixture of 650 ml of ethanol and 650 ml of concentrated acetic acid. This solution is combined with 167 g of iron powder and the mixture is heated under reflux for 90 minutes.

The reaction mixture is allowed to cool and poured into 5 l of ice water, filtered over kieselguhr, the latter is washed with diethyl ether and ethyl acetate, the organic phase is separated and the aqueous phase is extracted three times with ethyl acetate. The combined organic phases are washed with saturated sodium carbonate solution, dried, and concentrated under vacuum. The residue is recrystallized from ethanol, thus producing 32.4 g of 7-methoxyindole-2-carboxylic acid ethyl ester, mp 113° C.

B. 11.0 g of 7-methoxyindole-2-carboxylic acid ethyl ester is reacted with boron tribromide under the conditions of Example 1(B) and worked up. Yield after recrystallization from ethanol: 4.7 g of 7-hydroxyindole-2-carboxylic acid ethyl ester, mp 195°–200° C.

C. Under the conditions of Example 3(A), 4.1 g of 7-hydroxyindole-2-carboxylic acid ethyl ester is reacted with 3.0 g of tert-butylaminoacetonitrile hydrochloride and worked up, yielding 1.75 g of 4-tert-butylaminoacetyl-7-hydroxyindole-2-carboxylic acid ethyl ester hydrochloride, decomposition point 272° C.

D. Under the conditions of Example 1(D), 1.0 g of 4-tert-butylaminoacetyl-7-hydroxyindole-2-carboxylic acid ethyl ester hydrochloride is reacted and worked up, thus obtaining after recrystallization from ethanol 573 mg of 4-(2-tert-butylamino-1-hydroxyethyl)-7-hydroxyindole-2carboxylic acid ethyl ester hydrochloride, decomposition point 168°–170° C.

EXAMPLE 8

A. A suspension of 6.0 g of 7-methoxyindole-2carboxylic acid in 100 ml of toluene is combined with 4.3 ml of thionyl chloride; the mixture is heated under stirring for 3 hours to 90° C., then concentrated under vacuum. The residue is combined with 50 ml of n-butanol and heated for one hour under reflux Then the mixture is evaporated to dryness under vacuum, the oily residue is boiled with 60 ml of petroleum ether, the clear solution is decanted from the dark residue, and cooling of the solution yields 4.1 g of 7-methoxyindole-2-carboxylic acid n-butyl ester, mp 66°–69° C.

B. 4.1 g of 7-methoxyindole-2-carboxylic acid n-butyl ester is reacted with boron tribromide under the conditions of Example 1(B) and worked up, thus obtaining, after recrystallization from diisopropyl ether, 2.1 g of 7-hydroxyindole-2-carboxylic acid n-butyl ester mp 142°–144° C.

C. Under ice cooling and agitation, 818 mg of tert-butylaminoacetonitrile hydrochloride and 1.2 g of 7-hydroxyindole-2-carboxylic acid n-butyl ester are added to a solution of 2.7 g of aluminum chloride in 20 ml of nitrobenzene. Then gaseous hydrogen chloride is introduced into the mixture at 0° to 3° C. for 7 hours, the reaction mixture is stirred for 16 hours at 0°–3° C., and then poured into ice water. The mixture is agitated for 10 minutes and then the precipitate is vacuum-filtered. The precipitate is recrystallized from isopropanol, thus obtaining 765 mg of 4-tert-butylaminoacetyl-7-hydroxyindole-2-carboxylic acid n-butyl ester hydrochloride, decomposition point 203°–208° C.

D. Under the conditions of Example 3(B), 766 mg of 4-tert-butylaminoacetyl-7-hydroxyindole-2-carboxylic acid n-butyl ester hydrochloride is hydrogenated and worked up, thus producing 640 mg of 4-(2-tert-butylamino-1-hydroxyethyl)-7-hydroxyindole-2-carboxylic acid n-butyl ester hydrochloride, decomposition point 148°–149° C.

EXAMPLE 9

A. Under the conditions of Example 8(A), 8 g of 7-methoxyindole-2-carboxylic acid is converted into the acid chloride and the latter is reacted with isobutanol. After working up of the reaction product and recrystallization from petroleum ether, 6.2 g of 7-methoxyindole-2-carboxylic acid isobutyl ester is obtained, mp 100°–101° C.

B. Under the conditions of Example 1(B), 5 g of 7-methoxyindole-2-carboxylic acid isobutyl ester is reacted and worked up, thus obtaining after recrystallization from isobutanol 2.23 g of 7-hydroxyindole-2-carboxylic acid isobutyl ester, mp 185°–187° C.

C. 1.0 g of 7-hydroxyindole-2-carboxylic acid isobutyl ester is reacted under the conditions of Example 8(C) with 682 mg of tert-butylaminoacetonitrile hydrochloride and worked up, thus obtaining 728 mg of 4-tert-butylaminoacetyl-7-hydroxyindole-2-carboxylic acid isobutyl ester hydrochloride, decomposition point 220°–225° C.

D. Under the conditions of Example 3(B), 1.1 g of 4-tert-butylaminoacetyl-7-hydroxyindole-2-carboxylic acid isobutyl ester hydrochloride is hydrogenated and worked up, thus producing 960 mg of 4-(2-tert-butylamino-1-hydroxyethyl)-7-hydroxyindole-2-carboxylic acid isobutyl ester hydrochloride, which decomposes starting at 135° C.

EXAMPLE 10

A-1. 10.3 g of 7-methoxyindole-2-carboxylic acid methyl ester is reacted under the conditions of Example 1(C) with 7.5 g of tert-butylaminoacetonitrile hydrochloride and worked up, yielding, after recrystallization from 1,2-dimethoxyethane, 8.0 g of 4-tert-butylaminoacetyl-7-methoxyindole-2-carboxylic acid methyl ester hydrochloride, decomposition point 189°–191° C.

A-2. A solution of 1.02 g of 7-methoxyindole-2carboxylic acid methyl ester in 25 ml of dichloromethane is combined with 2 g of aluminum chloride and 0.65 ml of bromoacetyl bromide and the mixture is heated for 3 hours under reflux. The reaction mixture is allowed to cool and poured into 100 ml of a mixture of equal parts of ice water and concentrated hydrochloric acid. The organic phase is separated, concentrated to dryness under vacuum, and recrystallization from acetonitrile yields 650 mg of 4-bromoacetyl-7-methoxyindole-2-carboxylic acid methyl ester, mp 197°–201° C.

A solution of 300 mg of 4-bromoacetyl-7-methoxyindole-2-carboxylic acid methyl ester in 5 ml of tetrahydrofuran is combined with 0.3 ml of tert-butylamine and the mixture is stirred for 4 hours at room temperature. The thus-precipitated tert-butylamine hydrochloride is then vacuum-filtered and the filtrate evaporated to dryness. The residue is dissolved in 20 ml of dimethylformamide, applied to 10 g of silica gel, and chromatographed on 75 g of silica gel with toluene-glacial acetic acid-water 10:10:1. The fraction containing the product of this process is concentrated, taken up in 5 ml of water under heating, and rendered alkaline with concentrated ammonia. The resultant precipitate is vacuum-filtered, dissolved in 5 ml of ethanol, combined with ethereal hydrochloric acid until turbidity sets in, and cooled to about 0° C. The thus-obtained crystallized product is vacuum-filtered, dried, and the product is 52 mg of 4-tert-butylaminoacetyl-7-methoxyindole-2-carboxylic acid methyl ester hydrochloride, decomposition point 187°–189° C.

B. Under the conditions of Example 1(D), 8.0 g of 4-tert-butylaminoacetyl-7-methoxyindole-2-carboxylic acid methyl ester hydrochloride is hydrogenated and worked up, yielding 7.5 g of 4-(2-tert-butylamino-1-hydroxyethyl)-7-methoxyindole-2-carboxylic acid methyl ester hydrochloride, decomposition point 193°–194° C.

EXAMPLE 11

A. A solution of 53 g of sodium bisulfite in 125 ml of water is combined with 38 ml of 37% formaldehyde solution and the mixture is stirred for one hour at 60°–65° C. Then the mixture is allowed to cool to room temperature, 103.5 g of 3-benzylaminobutyric acid methyl ester is added dropwise thereto, and the mixture is agitated for 2 hours at the internal temperature (about 35° C.). Thereafter a solution of 25 g of sodium cyanide in 80 ml of water is added to the reaction mixture and the latter is stirred for another 2 hours whereupon it is allowed to stand for 16 hours at room temperature. The mixture is then extracted with diethyl ether, the ether extract is dried over sodium sulfate, the solvent is evaporated under vacuum, and the residue is distilled at 0.3 torr, thus obtaining 76 g of 3-(N-benzyl-N-cyanomethylamino) butyric acid methyl ester, bp 115°–130° C. at 0.3 torr.

B. Under the conditions of Example 1(C), 3.07 g of 7-hydroxyindole-2-carboxylic acid methyl ester is reacted with 4.1 g of 3-(N-benzyl-N-cyanomethylamino)-butyric acid methyl ester and worked up, yielding 1.35 g of 4-[N-benzyl-N-(2-methoxycarbonyl-1-methylethyl)aminoacetyl]-7-hydroxyindole-2-carboxylic acid ethyl ester hydrochloride, decomposition point 215°–220° C.

C. Under the conditions of Example 3(B), 300 mg of 4-[N-benzyl-N-(2-methoxycarbonyl-1-methylethyl)aminoacetyl]-7-hydroxyindole-2-carboxylic acid ethyl ester hydrochloride is hydrogenated, thus obtaining 185 mg of 4-[1-hydroxy-2-(2-methoxycarbonyl-1-methylethylamino)ethyl]-7-hydroxyindole-2-carboxylic acid ethyl ester hydrochloride, which decomposes above 100° C.

EXAMPLE 12

A. A solution of 106 g of sodium bisulfite in 250 ml of water is combined with 44 g of acetaldehyde and the mixture is stirred for one hour at 60°–65° C. The mixture is then cooled to room temperature, 73.1 g of tert-butylamine is added dropwise thereto, and the mixture is stirred for 2 hours at room temperature. Then a solution of 150 g of sodium cyanide in 160 ml of water is added to the reaction mixture, and the latter is stirred for another 2 hours and then allowed to stand at room temperature for 16 hours. The mixture is thereafter extracted with diethyl ether, the ether extract is dried over sodium sulfate, the solvent is evaporated under vacuum, and the residue is distilled at 14 torr, thus obtaining 73.5 g of 2-tert-butylaminopropionitrile, bp 61°–63° C. at 14 torr.

B. Under the conditions of Example 3(A), 2.05 g of 7-hydroxyindole-2-carboxylic acid ethyl ester is reacted with 1.38 g of 2-tert-butylaminopropionitrile and worked up, yielding 520 mg of 4-(2-tert-butylamino)-propionyl-7-hydroxyindole-2-carboxylic acid ethyl ester hydrochloride, decomposition point 180°–185° C.

C. Under the conditions of Example 3(B), 350 mg of 4-(2-tert-butylamino)propionyl-7-hydroxyindole-2-carboxylic acid ethyl ester hydrochloride is hydrogenated and worked up, thus obtaining 300 mg of 4-(2-tert-butylamino-1-hydroxypropyl)-7-hydroxyindole-2-carboxylic ethyl ester hydrochloride, decomposition point 110°–115° C.

EXAMPLE 13

A. Under the conditions of Example 3(A), 2.05 g of 7-hydroxyindole-2-carboxylic acid ethyl ester is reacted with 1.5 g of cyclohexylaminoacetonitrile and worked up, thus producing 1.0 g of 4-cyclohexylaminoacetyl-7-hydroxyindole-2-carboxylic acid ethyl ester hydrochloride, decomposition point 256°–259° C.

B.. Under the conditions of Example 3(B), 0.75 g of 4-cyclohexylaminoacetyl-7-hydroxyindole-2-carboxylic acid ethyl ester hydrochloride is reacted and worked up, yielding 0.68 g of 4-(2-cyclohexylamino-1-hydroxyethyl)-7-hydroxyindole-2-carboxylic acid ethyl ester hydrochloride, decomposition point 180°–182° C.

EXAMPLE 14

A. A solution of 15.3 g of 3-methyl-2-nitrophenol in 150 ml of dimethylformamide is combined with 28 g of potassium carbonate and 34.2 g of benzyl bromide, and the mixture is stirred for 3 hours at 70°–80° C. Then the inorganic salts are vacuum-filtered, washed with dichloromethane, and the filtrate evaporated under vacuum. The residue is distilled in a bulb tube at a bath temperature of 120° C. and at 0.01 torr, thus obtaining 23.2 g of 3-benzyloxy-2-nitrotoluene as an oil.

B. Under agitation, 26.3 g of oxalic acid diethyl ester and, 15 minutes later, a solution of 21.9 g of 3-benzyloxy-2-nitrotoluene in 30 ml of diethyl ether are added dropwise to a suspension of 9 g of potassium ethanolate in 200 ml of diethyl ether. The reaction mixture is heated for 20 hours under reflux; the thus-separated potassium salt of 3-benzyloxy-2-nitrophenyl-pyruvic acid ethyl ester is vacuum-filtered and washed with diethyl ether. The salt is then dissolved in a mixture of 200 ml of ethanol and 200 ml of concentrated acetic acid, the solution is combined with 50 g of powdered iron and heated under reflux for 90 minutes. The reaction mixture is allowed to cool, poured into 1 liter of ice water, filtered over kieselguhr, and the kieselguhr washed with diethyl ether. The organic phase is separated and the aqueous phase is extracted three times with diethyl ether. The combined organic phases are washed with saturated sodium carbonate solution, dried, and concentrated under vacuum. The residue is recrystallized from ethanol, thus obtaining 9.6 g of 7-benzyloxyindole-2-carboxylic acid ethyl ester, mp 82°–83° C.

C. One gram of 10% palladium catalyst on active carbon is added to a solution of 22.2 g of 7-benzyloxyindole-2-carboxylic acid ethyl ester in 500 ml of ethanol and the mixture is hydrogenated for 1 hour with shaking under normal pressure. The reaction solution is then filtered and the filtrate evaporated to dryness under vacuum. The residue is recrystallized from ethanol, yielding 13.3 g of 7-hydroxyindole-2-carboxylic acid ethyl ester, mp 197°–199° C.

D. Under ice cooling, gaseous hydrogen chloride is introduced for 15 minutes into a solution of 840 mg of cyclopropylaminoacetonitrile in 40 ml of dioxane. Then 5.6 g of aluminum chloride is added, a solution of 2.05 g of 7-hydroxyindole-2-carboxylic acid ethyl ester in 20 ml of dioxane is added dropwise to the mixture, and gaseous hydrogen chloride is again introduced under ice cooling for 2 hours. The reaction mixture is thereafter stirred for 16 hours at +5° C., poured into ice water, stirred for another 20 minutes, and then the thus-separated precipitate is vacuum-filtered. The precipitate is extracted by boiling with ethanol, the remaining residue is dried, and the product is 1.2 g of 4-cyclopropylaminoacetyl 7-hydroxyindole-2-carboxylic acid ethyl ester hydrochloride, decomposition point 255°–258° C.

E. A solution of 504 mg of 4-cyclopropylaminoacetyl-7-hydroxyindole-2-carboxylic acid ethyl ester hydrochloride in 200 ml of methanol is combined with 100 mg of 10% palladium catalyst on active carbon, and the mixture is hydrogenated for 2 hours under shaking and normal pressure. The reaction mixture is then filtered and the filtrate concentrated to dryness. The residue is stirred up with 10 ml of cold water, the undissolved matter is vacuum-filtered and dried at 50° C. under vacuum, thus obtaining 275 mg of 4-(1-cyclopropylamino-2-hydroxyethyl)7-hydroxyindole-2-carboxylic acid ethyl ester hydrochloride, decomposition point 195°–197° C.

EXAMPLE 15

Under the conditions of Example 14(D), 1.91 g of 7-hydroxyindole-2-carboxylic acid methyl ester and 2.4 g of 2-(4-methoxyphenyl)-1-methylethylaminoacetonitrile are reacted and worked up, thus obtaining 1.55 g of 4-[2-(4-methoxyphenyl)-1-methylethylaminoacetyl]-7-hydroxyindole-2-carboxylic acid methyl ester hydrochloride, decomposition point 253°–255° C.

One gram of this product is hydrogenated and worked up under the conditions of Example 14(E), thus obtaining 834 mg of 4-{1-hydroxy-2-[2-(4-methoxyphenyl)-1-methylethylamino]ethyl}-7-hydroxyindole-2-carboxylic acid methyl ester hydrochloride, decomposition point 120° C.

EXAMPLE 16

300 mg of 4-{1-hydroxy-2-[2-(4-methoxyphenyl)-1-methylethylamino]ethyl}-7-hydroxyindole-2-carboxylic acid methyl ester hydrochloride is dissolved in 5 ml of N sodium hydroxide solution and stirred for one hour at room temperature. The reaction mixture is then cooled in an ice bath, acidified with concentrated acetic acid, stirred for another 10 minutes, and the crystallized product is vacuum filtered, washed with water and acetone, and dried under vacuum, thus obtaining 185 mg of 4-{1-hydroxy-2-[2-(4-methoxyphenyl)-1-methylethylamino]}ethyl-7-hydroxyindole-2-carboxylic acid, decomposition point 250° C.

EXAMPLE 17

A. 20 g of 3-benzyloxy-2-nitrophenylpyruvic acid ethyl ester is suspended in 100 ml of ethanol, combined with 28 g of methyl iodide, and heated under reflux for 2 hours. The reaction mixture is allowed to cool, concentrated to dryness, diluted with water, and extracted three times with diethyl ether.

The organic phases are combined, dried, and concentrated. The oily residue is dissolved in a mixture of 160 ml of concentrated acetic acid and 160 ml of ethanol, warmed to 60° C., combined with 36 g of powdered iron in incremental portions, and stirred at 60°–70° C. for 2 hours.

The reaction mixture is allowed to cool overnight, then decanted from the iron residue; the latter is extracted three times with diethyl ether. The organic phases are combined and dried. After filtration over active carbon, the filtrate is evaporated to dryness, the residue is recrystallized from acetonitrile, and the resultant product is 3.5 g of 7-benzyloxy-3-methylindole-2-carboxylic acid ethyl ester, mp 109°–110° C.

B. Under the conditions of Example 14(C), 1.3 g of 7-benzyloxy-3-methylindole-2-carboxylic acid ethyl ester is hydrogenated and worked up, thus obtaining 2.0 g of 7-hydroxy-3-methylindole-2-carboxylic acid ethyl ester, mp 187°–190° C.

C. Under the conditions of Example 14(D), 3 g of 7-hydroxy-3-methylindole-2-carboxylic acid ethyl ester and 2 g of tert-butylaminoacetonitrile hydrochloride are reacted and worked up, yielding 3.6 g of 4-tert-butylaminoacetyl-7-hydroxy-3-methylindole-2-carboxylic acid ethyl ester hydrochloride.

D. Under the conditions of Example 14(E), 3 g of 4-tert-butylaminoacetyl-7-hydroxy-3-methylindole-2-carboxylic acid ethyl ester hydrochloride is hydrogenated and worked up, yielding 1.9 g of 4-(1-hydroxy-2-tert-butylaminoethyl)-7-hydroxy-3-methylindole-2-carboxylic acid ethyl ester hydrochloride, decomposition point 153°–156° C.

EXAMPLE 18

Under the conditions of Example 16, 1 g of 4-(1-hydroxy-2-tert-butylaminoethyl)-7-hydroxy-3-methylindole-2-carboxylic acid ethyl ester hydrochloride is hydrolyzed and worked up, thus obtaining 560 mg of 4-(1-hydroxy-2-tert-butylaminoethyl)-7-hydroxy-3-methylindole-2-carboxylic acid, decomposition point 230°–231° C.

EXAMPLE 19

A. A solution of 7-benzyloxyindole-2-carboxylic acid ethyl ester in 600 ml of tetrahydrofuran and 200 ml of methanol is combined with 500 ml of 2N sodium hydroxide solution and stirred for 3 hours at room temperature. The reaction mixture is then acidified under ice cooling with 10% hydrochloric acid and extracted twice with ethyl acetate. The combined organic phases are dried, treated with active carbon, and concentrated. The residue is recrystallized from toluene, thus producing 35 g of 7-benzyloxyindole-2-carboxylic acid, mp 166°–168° C.

B. 5.3 g of 7-benzyloxyindole-2-carboxylic acid is suspended in 80 ml of dichloromethane and combined in succession with 4.1 g of dicyclohexylcarbodiimide, 1.9 g of phenol, and 300 mg of 4-pyrrolidinopyridine. The reaction mixture is stirred for 18 hours at room temperature, the resultant precipitate is filtered off, and the filtrate is extracted twice with water, twice with 5% acetic acid, and twice with water. The organic phase is dried, treated with active carbon, and concentrated. The residue is chromatographed over a silica gel column with chloroform, thus obtaining 5.5 g of 7-benzyloxyindole-2-carboxylic acid phenyl ester as a viscous oil.

C. Under the conditions of Example 14(C), a solution of 5.4 g of 7-benzyloxyindole-2-carboxylic acid phenyl ester in a mixture of 50 ml of methanol and 30 ml of tetrahydrofuran is hydrogenated and worked up, yielding 3.5 g of 7-hydroxyindole-2-carboxylic acid phenyl ester, mp 156°–157° C.

D. Under the conditions of Example 14(D), 2.5 g of 7-hydroxyindole-2-carboxylic acid phenyl ester and 1.5 g of tert-butylaminoacetonitrile hydrochloride are reacted and worked up, thus obtaining 2.2 g of 4-tert-butylaminoacetyl-7-hydroxyindole-2carboxylic acid phenyl ester hydrochloride, decomposition point 276° C.

E. Under the conditions of Example 14(E), 1.5 g of 4-tert-butylaminoacetyl-7-hydroxyindole-2-carboxylic acid phenyl ester hydrochloride is hydrogenated in a mixture of 40 ml of methanol and 40 ml of tetrahydrofuran and worked up, thus producing 1.35 g of 4-(2-tert-butylamino-1-hydroxy-ethyl)-7-hydroxyindole-2-carboxylic acid phenyl ester hydrochloride, decomposition point 165°–166° C.

EXAMPLE 20

A. 10.6 g of 7-benzyloxyindole-2-carboxylic acid is suspended in 100 ml of toluene, combined with 5.8 ml of thionyl chloride, and heated for 2½ hours under agitation to 100° C. The reaction mixture is allowed to cool, concentrated to dryness, the residue is combined twice with toluene and in each case evaporated to dryness under vacuum. The resultant oil is dissolved in 30 ml of toluene and added dropwise under agitation at room temperature to a solution of 7.1 g of dimethylaminoethanol in 80 ml of toluene. After one hour, the reaction mixture is evaporated to dryness; the residue is poured into water and extracted with methyl acetate. The organic phases are combined, dried, treated with active carbon, and evaporated to dryness. The residue is recrystallized from isopropanol, thus obtaining 9.1 g of 7-benzyloxyindole-2-carboxylic acid 2-dimethylaminoethyl ester, mp 113°–115° C.

B. Under the conditions of Example 14(C), 9 g of 7-benzyloxyindole-2-carboxylic acid 2-dimethylaminoethyl ester is hydrogenated in a mixture of 50 ml of methanol and 50 ml of tetrahydrofuran and worked up, yielding 3.7 g of 7-hydroxyindole-2-carboxylic acid 2-dimethylaminoethyl ester, mp 149°–152° C.

C. Under the conditions of Example 14(D), 2.5 g of 7-hydroxyindole-2-carboxylic acid 2-dimethylaminoethyl ester and 1.5 g of tert-butylaminoacetonitrile hydrochloride are reacted and worked up, thus obtaining 2.6 g of 4-tert-butylaminoacetyl-7-hydroxyindole-2-carboxylic acid 2-dimethylaminoethyl ester hydrochloride, decomposition point 266°–268° C.

D. Under the conditions of Example 14(E), 869 mg of 4-tert-butylaminoacetyl-7-hydroxyindole-2-carboxylic acid 2-dimethylaminoethyl ester hydrochloride is hydrogenated and worked up, yielding 510 mg of 4-(2-tert-butyl-amino-1-hydroxyethyl)-7-hydroxyindole-2-carboxylic acid 2-dimethylaminoethyl ester hydrochloride, decomposition point 176° C.

EXAMPLE 21

A. A solution of 5.37 g of 7-benzyloxyindole-2carboxylic acid in 20 ml of dimethylformamide is combined with 2.2 g of triethylamine and 3.6 g of bromomethyl acetate, and the mixture is stirred for 5 hours at room temperature. The reaction mixture is introduced into 150 ml of ice water, the precipitate is vacuum-filtered, dissolved in 300 ml of chloroform, and washed with 10% sodium bicarbonate solution and water. The organic phase is dried, concentrated to dryness, the residue recrystallized from ethyl acetate, and the product is 3.8 g of 7-benzyloxyindole-2carboxylic acid acetoxymethyl ester, mp 170°–171° C.

B. Under the conditions of Example 14(C), 2.27 g of 7-benzyloxyindole-2-carboxylic acid acetoxymethyl ester in 40 ml of tetrahydrofuran is hydrogenated and worked up, thus obtaining 1.43 g of 7-hydroxyindole-2-carbocylic acid acetoxymethyl ester, mp 159°–160° C.

C. Under the conditions of Example 14(D), 2.5 g of 7-hydroxyindole-2-carboxylic acid acetoxymethyl ester is reacted with 1.48 g of tert-butylaminoacetonitrile hydrochloride and worked up, thus obtaining 3.43 g of 4-tert-butylaminoacetyl-7-hydroxyindole-2-carboxylic acid acetoxymethyl ester hydrochloride, decomposition point 261° C.

D. Under the conditions of Example 14(E), 300 mg of 4-tert-butylaminoacetyl-7-hydroxyindole-2-carboxylic acid acetoxymethyl ester hydrochloride is hydrogenated and worked up, yielding 202 mg of 4-(2-tert-butylamino-1-hydroxyethyl)-7-hydroxyindole-2-carboxylic acid acetoxymethyl ester hydrochloride, decomposition point 168° C.

EXAMPLE 22

A. A solution of 12.3 g of 3-(N-benzyl-N-cyanomethylamino)butyric acid methyl ester in a mixture of 100 ml of water and 25 ml of 65% nitric acid is heated under agitation for 2 hours to 80° C. The reaction mixture is allowed to cool, combined with solid sodium acetate until a weakly acidic reaction is obtained, and extracted three times with diethyl ether. The combined organic phases are extracted twice with 10% aqueous sodium carbonate solution, the combined aqueous phases are acidified with acetic acid and extracted three times with dichloromethane. The combined organic phases are dried, treated with active carbon, evaporated to dryness, and the residue triturated with pentane. The thus-produced crystals are vacuum-filtered. Yield: 7.8 g of 3-(N-benzyl-N-cyanomethylamino)butyric acid, mp 71°–73° C.

B. A solution of 4.6 g of 3-(N-benzyl-N-cyanomethylamino)butyric acid in 100 ml of n-butanol is combined with 0.5 ml of concentrated sulfuric acid and the mixture is heated for 4 hours on a water trap under reflux. The reaction mixture is allowed to cool, concentrated to dryness, and the residue dissolved in diethyl ether. The ether solution is washed with 10% sodium bicarbonate solution and saturated sodium chloride solution, dried, and evaporated to dryness. The oily residue is distilled in a bulb tube at 85°–105° C. and 0.01 torr, thus obtaining 1.17 g of 3-(N-benzyl-N-cyanomethylamino)butyric acid n-butyl ester as an oil.

C. A suspension of 10.8 g of 7-benzyloxyindole-2-carboxylic acid in 180 ml of toluene is combined with 5.8 ml of thionyl chloride and the mixture is heated under agitation for 2 hours to 90° C. The reaction mixture is then concentrated under vacuum, the residue combined with 150 ml of n-butanol, and the mixture is heated for one hour under reflux. Subsequently the mixture is concentrated to dryness, the residue is recrystallized from isopropanol, and the product is 7.4 g of 7-benzyloxyindole-2-carboxylic acid n-butyl ester, mp 77°–78° C.

D. Under the conditions of Example 14(C), a solution of 5.8 g of 7-benzyloxyindole-2-carboxylic acid n-butyl ester in 200 ml of methanol is hydrogenated and worked up, thus obtaining 3.2 g of 7-hydroxyindole-2-carboxylic acid n-butyl ester, mp 150°–151° C.

E. Under the conditions of Example 14(D), 700 ml of 7-hydroxyindole-2-carboxylic acid n-butyl ester and 865 mg of 3-(N-benzyl-N-cyanomethylamino)butyric acid n-butyl ester are reacted and worked up, thus obtaining 495 mg of 4-(2-n-butoxycarbonyl-1-methylethylaminoacetyl)-7-hydroxyindole-2-carboxylic acid n-butyl ester hydrochloride, decomposition point 200°–203° C.

F. Under the conditions of Example 14(E), 380 mg of 4-(2-n-butoxycarbonyl-1-methylethylaminoacetyl)-7-hydroxyindole-2-carboxylic acid n-butyl ester hydrochloride in 10 ml of methanol and 5 ml of tetrahydrofuran is hydrogenated and worked up, yielding 185 mg of 4-[1-hydroxy-2-(2-n-butoxycarbonyl-1-methylethylamino)ethyl]-7-hydroxyindole-2-carboxylic acid n-butyl ester hydrochloride, decomposition point 75°–84° C.

EXAMPLE 23

A. 48.8 g of 4-[N-benzyl-N-(2-methoxycarbonyl-1-methylethyl)aminoacetyl]-7-hydroxyindole-2-carboxylic acid ethyl ester hydrochloride, 41.4 g of potassium carbonate, and 25 ml of benzyl bromide are heated under reflux for 6 hours in 900 ml of acetone. After cooling, the reaction mixture is concentrated to dryness, the residue is taken up in ethyl acetate and saturated sodium bicarbonate solution, the organic phase is separated and extracted three times with saturated sodium bicarbonate solution. The organic phase is washed with water, dried, concentrated, and the residue is recrystallized from ethyl acetate/n-hexane, thus obtaining 42.5 g of 4-[N-benzyl-N-(2-methoxycarbonyl-1-methylethyl)aminoacetyl]-7-benzyloxyindole-2-carboxylic acid ethyl ester, mp 120°–123° C.

B. 38 g of 4-[N-benzyl-N-(2-methoxycarbonyl-1-methylethyl)aminoacetyl]-7-benzyloxyindole-2-carboxylic acid ethyl ester is stirred at room temperature for 4 hours in a mixture of 1 liter of tetrahydrofuran, 1 liter of methanol, and 350 ml of 2N sodium hydroxide solution. The reaction mixture is then acidified with 2N hydrochloric acid, concentrated until the onset of crystallization, cooled in an ice bath, and the resultant crystals are vacuum-filtered, thus producing 25.8 g of 4-[N-benzyl-N-(2-carboxy-1-methylethyl)aminoacetyl]-7-benzyloxyindole-2-carboxylic acid hydrochloride, decomposing from 150° C. on.

C. Under the conditions of Example 21(A), 5 g of 4-[N-benzyl-N-(2-carboxy-1-methylethyl)aminoacetyl]-7-benzyloxyindole-2-carboxylic acid hydrochloride is reacted with 1.6 g of chloromethylmethyl ether and worked up. Treatment of the crude product with dioxane/acetic acid yields 4.2 g of 4-[N-benzyl-N-(2-methoxymethoxycarbonyl-1-methylethyl)aminoacetyl]-7-benzyloxyindole-2-carboxylic acid methoxymethyl ester acetate, decomposition point 118°–122° C.

D. Under the conditions of Example 14(E), 3.5 g of 4-[N-benzyl-N-(2-methoxymethoxycarbonyl-1-methylethyl)aminoacetyl]-7-benzyloxyindole-2-carboxylic acid methoxymethyl ester acetate is hydrogenated and worked up, yielding 2.1 g of 4-[1-hydroxy-2-(2-methoxymethoxycarbonyl-1-methylethylamino)e- thyl]-7-hydroxyindole-2-carboxylic acid methoxymethyl ester acetate, decomposition point 110° C.

EXAMPLE 24

A. Under the conditions of Example 21(A), 5.14 g of 4-[N-benzyl-N-(2-carboxy-1-methylethyl)aminoacetyl]-7-benzyloxyindole-2-carboxylic acid hydrochloride is reacted with 3.06 g of bromomethyl acetate and worked up, thus obtaining, after treatment of the crude product with dioxane/acetic acid, 2.80 g of 4-[N-benzyl-N-(2-acetoxymethoxycarbonyl-1-methylethyl)aminoacetyl]-7-benzyloxyindole-2-carboxylic acid acetoxymethyl ester acetate, decomposition point 97°–101° C.

B. Under the conditions of Example 14(E), 2.50 g of 4-[N-benzyl-N-(2-acetoxymethoxycarbonyl-1-methylethyl)aminoacetyl]-7-benzyloxyindole-2-carboxylic acid acetoxymethyl ester acetate is hydrogenated and worked up, thus obtaining 1.10 g of 4-[1-hydroxy-2-(2-acetoxymethoxycarbonyl-1-methylethylamino)ethyl]-7-hydroxyindole-2-carboxylic acid acetoxymethyl ester acetate, decomposition point 82° C.

EXAMPLE 25

A. Under the conditions of Example 21(A), 5.14 g of 4-[N-benzyl-N-(2-carboxy-1-methylethyl)aminoacetyl]-7-benzyloxyindole-2-carboxylic acid hydrochloride is reacted with 3.00 g of 2-dimethylaminoethyl chloride hydrochloride and worked up, thus producing, after treatment of the crude product with dioxane/acetic acid, 1.80 g of 4-{N-benzyl-N-[2-(2-dimethylaminoethoxycarbonyl)-1-methylethyl]-aminoacetyl}-7-benzyloxyindole-2-carboxylic acid 2-dimethylaminoethyl ester acetate, decomposition point 122°–125° C.

B. Under the conditions of Example 14(E), 1.50 g of 4-{N-benzyl-N-[2-(2-dimethylaminoethoxycarbonyl)-1-methylethyl]aminoacetyl}-7-benzyloxyindole-2-carboxylic acid 2-dimethylaminoethyl ester acetate is hydrogenated and worked up, yielding 0.40 g of 4-{1-hydroxy-2-[2-(2-dimethylaminoethoxycarbonyl-1-methylethylamino)ethyl]}-7-hydroxyindole-2-carboxylic acid 2-dimethylaminoethyl ester acetate, decomposition point 102° C.

EXAMPLE 26

A. Under the conditions of Example 21(A), 5.14 g of 4-[N-benzyl-N-(2-carboxy-1-methylethyl)aminoacetyl]-7-benzyloxyindole-2-carboxylic acid hydrochloride is reacted with 4.50 g of 2-morpholinoethyl chloride hydrochloride and worked up, thus obtaining, after treatment of the crude product with dioxane/acetic acid, 2.20 g of 4-{N-benzyl-N-[2-(2-morpholinoethoxycarbonyl)-1-methylethyl]aminoacetyl}-7-benzyloxyindole-2-carboxylic acid 2-morpholinoethyl ester acetate, decomposition point 133°–136° C.

B. Under the conditions of Example 14(E), 2.00 g of 4-{N-benzyl-N-[2-(2-morpholinoethoxycarbonyl)-1-methylethyl]aminoacetyl}-7-benzyloxyindole-2-carboxylic acid 2-morpholinoethyl ester acetate is hydrogenated and worked up, thus obtaining 0.80 g of 4-{1-hydroxy-2-[2-(2-morpholinoethoxycarbonyl)-1-methylethylamino]ethyl}-7-hydroxyindole-2-carboxylic acid 2-morpholinoethyl ester acetate, decomposition point 120° C.

EXAMPLE 27

A. Under ice cooling, hydrogen chloride is introduced for 15 minutes into a solution of 7.6 ml of chloroacetonitrile in 100 ml of dioxane. Then 53 g of aluminum chloride is added to the reaction mixture. Under ice cooling, hydrogen chloride is once more introduced for 15 minutes and, while continuing the introduction of hydrogen chloride, a solution of 7-hydroxyindole-2-carboxylic acid ethyl ester in 200 ml of dioxane is added dropwise within 30 minutes to the mixture. The reaction mixture is allowed to stand for 2½ hours at 0° C., then poured into 2 l of ice water, and stirred for 1½ hours at room temperature. The resultant precipitate is vacuumfiltered, washed with water, recrystallized from methanol, and the product is 22.2 g of 4-chloroacetyl-7-hydroxyindole-2-carboxylic acid ethyl ester, mp 230°–232° C. (decomposition).

B. 2.8 g of 4-chloroacetyl-7-hydroxyindole-2-carboxylic acid ethyl ester is combined with 1.5 ml of allylamine and 15 ml of absolute dimethyl sulfoxide and stirred at room temperature for one hour. Then 150 ml of 2N hydrochloric acid is added to the reaction mixture, the immediately formed precipitate is vacuum-filtered, and the filtrate is allowed to stand and thus yields, in crystalline form, 1.5 g of 4-allylaminoacetyl-7-hydroxyindole-2-carboxylic acid ethyl ester hydrochloride, mp 264°–265° C. (decomposition).

C. 680 mg of 4-allylaminoacetyl-7-hydroxyindole-2-carboxylic acid ethyl ester hydrochloride is combined with 100 ml of water and 50 ml of methanol and warmed to 40° C. Within 4 hours, 4 g of sodium borohydride is added in incremental portions to this mixture, the latter is cooled with ice, acidified to pH 5 with 5N acetic acid, and extracted twice with diethyl ether.

The aqueous phase is combined with sodium bicarbonate and extracted three times with n-butanol/ethyl acetate (1+3). The organic phase is concentrated, the residue is dissolved in 25 ml of 2N acetic acid, extracted three times with diethyl ether, the aqueous phase is combined with sodium bicarbonate, and extracted three times with ethyl acetate. The organic phase is dried, concentrated under vacuum, and the residue is chromatographed over a silica gel column (eluent: toluene/acetic acid/methanol/water (6+4+2+0.6). Recrystallization from methanol/acetic acid/diisopropyl ether yields 260 mg of 7-hydroxy-4-(1-hydroxy-2-allylaminoethyl)indole-2-carboxylic acid ethyl ester acetate, mp 129°–130° C. (decomposition).

EXAMPLE 28

A. 3.4 g of 4-chloroacetyl-7-hydroxyindole-2-carboxylic acid ethyl ester is combined with 4.2 g of 1-(4-benzyloxyphenyl)propyl-2-amine hydrochloride, 4.2 ml of triethylamine, and 15 ml of dimethyl sulfoxide and stirred for 4 hours at room temperature. The mixture is then combined with 200 ml of 2N hydrochloric acid and 100 ml of ethyl acetate; the crystallized product is vacuum-filtered and washed with 2N hydrochloric acid and ethyl acetate. Yield: 1.8 g of 4-[2-(4-benzyloxyphenyl)-1-methylethylaminoacetyl]-7-hydroxyindole-2-carboxylic acid ethyl ester hydrochloride, decomposition point 248° C. (from methanol/ethyl acetate).

B. 209 mg of 4-[2-(4-benzyloxyphenyl)-1-methylethyl-aminoacetyl]-7-hydroxyindole-2-carboxylic acid ethyl ester hydrochloride is hydrogenated in 20 ml of methanol for 2.5 hours at room temperature and under normal pressure in the presence of 42 mg of 10% palladium-carbon. The mixture is filtered, the filtrate is concentrated under vacuum, and the residue is recrystallized from acetone/diethyl ether, thus obtaining 115 mg of 4-{1-hydroxy-2-[2-(4-hydroxyphenyl)-1-methylethylamino]ethyl}-7-hydroxy-indole-2-carboxylic acid ethyl ester hydrochloride, decomposition point 110° C.

EXAMPLE 29

A. Under the conditions of Example 28, 2.57 g of 4-chloroacetyl-7-hydroxyindole-2-carboxylic acid ethyl ester is reacted with 2.35 g of 3-benzylamino-3-methylbutyric acid ethyl ester and worked up, yielding 0.75 g of 4-[N-benzyl-N-(2-ethoxycarbonyl-1,1-dimethylethyl)aminoacetyl]-7-hydroxyindole-2-carboxylic acid ethyl ester hydrochloride, decomposition point 210°–212° C.

B. Under the conditions of Example 14(E), 4-[N-benzyl-N-(2-ethoxycarbonyl-1,1-dimethylethyl)aminoacetyl]-7-hydroxyindole-2-carboxylic acid ethyl ester is hydrogenated and worked up, thus obtaining 320 mg of 4-[1-hydroxy-(2-ethoxycarbonyl-1,1-dimethylethylamino)ethyl]-7-hydroxyindole-2-carboxylic acid ethyl ester, mp 175°–178° C.

EXAMPLE 30

A. 1.8 g of 4-chloroacetyl-7-hydroxyindole-2-carboxylic acid ethyl ester and 1.8 g of N,N'-dibenzylhexamethylenediamine are stirred in 25 ml of absolute dimethyl sulfoxide for 2 hours at room temperature, then combined with ethyl acetate, and the thus-precipitated crystallized product is vacuum-filtered. The mother liquor is concentrated. The residue is chromatographed over a silica gel column (eluent: methanol/chloroform-/acetone 4+6+2) and recrystallized from acetone, 1N ethereal hydrochloric acid/diethyl ether. Yield: 775 mg of N,N'-hexamethylenebis[4-(N-benzylaminoacetyl)-7-hydroxyindole-2-carboxylic acid ethyl ester] dihydrochloride, decomposition point 219°–221° C.

B. 687 mg of N,N'-hexamethylenebis[4-(N-benzylaminoacetyl-7-hydroxyindole-2-carboxylic acid ethyl ester] dihydrochloride in 80 ml of methanol is combined with 500 mg of 10% palladium-carbon and hydrogenated for 36 hours at room temperature and under normal pressure. The catalyst is then filtered off, the mixture concentrated under vacuum, and the residue is recrystallized from methanol/ethyl acetate, thus obtaining 300 mg of N,N'-hexamethylenebis[4-(2-amino-1-hydroxyethyl)-7-hydroxyindole-2-carboxylic acid ethyl ester] dihydrochloride, decomposition point 142° C.

EXAMPLE 31

A. Under ice cooling, hydrogen chloride is introduced into 300 ml of dioxane for 15 minutes. Then 33 g of N-tert-butylaminoacetonitrile hydrochloride is added thereto and hydrogen chloride is introduced under ice cooling for another 30 minutes. The mixture is cooled to −30° C., 106 g of aluminum chloride is added, hydrogen chloride is introduced under ice cooling for another 30 minutes, and the mixture is combined with 41 g of 7-hydroxyindole-2-carboxylic acid ethyl ester in 300 ml of dioxane.

The reaction mixture is stirred under ice cooling and introduction of hydrogen chloride for 2 hours and then for another 3 hours under ice cooling. The precipitate is vacuum-filtered, washed with dioxane, and stirred for 3 hours with 700 ml of water and 50 ml of concentrated hydrochloric acid. The product is then vacuum-filtered, dried, and recrystallized from methanol/diethyl ether, thus obtaining 58.9 g of 4-(N-tert-butylaminoacetyl)-7-hydroxyindole-2-carboxylic acid ethyl ester hydrochloride, decomposition point 271° C.

B. 53.6 g of 4-(N-tert-butylaminoacetyl)-7-hydroxyindole-2-carboxylic acid ethyl ester hydrochloride is combined with 59.3 g of potassium carbonate, 63.6 ml of benzyl bromide, and 1000 ml of acetone and heated under reflux for 6 hours. The mixture is then concentrated under vacuum and the residue combined with ethyl acetate and saturated sodium bicarbonate solution. The organic phase is washed three times with sodium bicarbonate solution and once with water, dried over calcium sulfate, and concentrated. The residue is recrystallized twice from ethyl acetate/hexane, thus obtaining 47 g of 7-benzyloxy-4-(N-benzyl-N-tert-butylaminoacetyl)indole-2-carboxylic acid ethyl ester, mp 155°–157° C.

C. 10 g of 7-benzyloxy-4-(N-benzyl-N-tert-butylaminoacetyl)-2-indolecarboxylic acid ethyl ester is combined with 300 ml of tetrahydrofuran, 300 ml of methanol, and 100 ml of 2N sodium hydroxide solution and stirred for 4 hours at room temperature. Then 120 ml of 2N hydrochloric acid is added and the mixture concentrated until the onset of crystallization. The crystallized product is vacuum-filtered and the mother liquor once more concentrated. The resultant secondary crystallization product is combined with the first-obtained crystallized product, dried, and recrystallized from methanol/ethyl acetate, thus obtaining 8.8 g of 7-benzyloxy-4-(N-benzyl-N-tert-butylaminoacetyl)indole-2-carboxylic acid hydrochloride, decomposition point 158° C.

D. 1.00 g of 7-benzyloxy-4-(N-benzyl-N-tert-butylaminoacetyl)-2-indolecarboxylic acid hydrochloride, 1.4 ml of triethylamine, and 1.12 ml of the chloromethyl ester of trimethylacetic acid are combined with 15 ml of absolute dimethylformamide and stirred for 16 hours at room temperature. Then the mixture is concentrated, the residue dissolved in ethyl acetate, extracted three times with water, the organic phase is dried and concentrated, and the residue is chromatographed over an aluminum oxide column (activity stage II; eluent: cyclohexane/ethyl acetate 4+1). The product is recrystallized from diisopropyl ether/ethereal hydrochloric acid, yielding 0.7 g of 7-benzyloxy-4-(N-benzyl-N-tert-butylaminoacetyl)-2-indolecarboxylic acid trimethylacetoxymethyl ester hydrochloride, decomposition point 184°–185° C.

E. 609 mg of 7-benzyloxy-4-(N-benzyl-N-tert-butylaminoacetyl)-2-indolecarboxylic acid trimethylacetoxymethyl ester hydrochloride is combined with 30 ml of absolute tetrahydrofuran, 3 ml of methanol, and 0.5 ml of acetic acid and hydrogenated in the presence of 100 mg of 10% palladium-carbon for 10 hours at room temperature under normal pressure. The mixture is then concentrated, the residue is crystallized from methanol/diethyl ether, and the product is 300 mg of 7-hydroxy-4-(1-hydroxy-2-tert-butylaminoethyl)indole-2-carboxylic acid trimethylacetoxymethyl ester, decomposition point 173°–175° C.

EXAMPLE 32

A. 1.00 g of 7-benzyloxy-4-(N-benzyl-N-tert-butylaminoacetyl)-2-indolecarboxylic acid hydrochloride, 0.6 ml of chloromethylmethyl ether, 1.4 ml of triethylamine are dissolved in 20 ml of absolute dimethylformamide and stirred for one hour at 0° C. and for 16 hours at room temperature.

The mixture is then concentrated under vacuum, the residue is combined with ethyl acetate and water, the crystallized product is vacuum-filtered, and the yield is 680 mg of 7-benzyloxy-4-(N-benzyl-N-tert-butylaminoacetyl)-2-indolecarboxylic acid methoxymethyl ester, mp 178°–179° C. (from tetrahydrofuran/diisopropyl ether).

B. 617 mg of 7-benzyloxy-4-(N-benzyl-N-tert-butylaminoacetyl)-2-indolecarboxylic acid methoxymethyl ester is combined with 10 ml of methanol, 40 ml of absolute tetrahydrofuran, and 0.3 ml of acetic acid and hydrogenated and worked up as described in Example 31(E), thus obtaining 450 mg of 7-hydroxy-4-(1-hydroxy-2-tert-butylaminoethyl)indole-2-carboxylic acid methoxymethyl ester acetate, decomposition point 165°–170° C.

EXAMPLE 33

A. 1.00 g of 7-benzyloxy-4-(N-benzyl-N-tert-butylaminoacetyl)-2-indolecarboxylic acid hydrochloride is combined with 4 ml of absolute dimethylformamide and 8 ml of absolute tetrahydrofuran, cooled to −10° C., and combined with 0.52 ml of N-ethylmorpholine and, 5 minutes later, with 0.28 ml of isobutyl chloroformate. The mixture is allowed to stand at −5° C. for 30 minutes, 376 mg of aminoacetic acid methyl ester hydrochloride, 0.39 ml of triethylamine—dissolved in 4 ml of absolute dimethylformamide and 6 ml of absolute tetrahydrofuran—are added thereto, the mixture is stirred for 16 hours at room temperature, concentrated, the residue is taken up in ethyl acetate/water, and the aqueous phase is acidified with 1N hydrochloric acid and once again extracted with ethyl acetate. The combined organic phases are dried, concentrated, and chromatographed over an aluminum oxide column (activity stage II; eluent: methanol/chloroform 1+4), thus obtaining 600 mg of N-[7-benzyloxy-4-(N-benzyl-N-tert-butylaminoacetyl)-2-indolylcarbonyl]aminoacetic acid methyl ester, mp 151.5°–152.5° C. (from methanol/diisopropyl ether).

B. 300 mg of N-[7-benzyloxy-4-(N-benzyl-N-tert-butylaminoacetyl) butylaminoacetyl)-2-indolylcarbonyl]aminoacetic acid methyl ester is combined with 10 ml of methanol, 20 ml of absolute tetrahydrofuran, and 0.16 ml of acetic acid and hydrogenated and worked up as described in Example 31(E), thus producing 115 mg of N-[7-hydroxy-4-(1-hydroxy-2-tert-butylaminoethyl-2-indolylcarbonyl]aminoacetic acid methyl ester acetate, decomposition point 140° C.

EXAMPLE 34

A. 4 g of 7-benzyloxy-4-(N-benzyl-N-tert-butylaminoacetyl)-2-indolecarboxylic acid ethyl ester is combined with 75 ml of absolute tetrahydrofuran and 150 ml of diethyl ether and stirred under ice cooling for 9 hours with 1.2 g of lithium aluminum hydride. Then a small amount of water is added to the reaction mixture, the precipitate is vacuum-filtered, washed with ethyl acetate/diethyl ether, the combined filtrates are concentrated, and the residue is recrystallized from diisopropyl ether, thus obtaining 3.4 g of 2-(N-benzyl-N-tert-butylamino) -1-(7-benzyloxy-2-hydroxymethylindol-4-yl)ethanol, mp 135.5°–136.5° C.

B. 687 mg of 2-(N-benzyl-N-tert-butylamino)-1(7-benzyloxy-2-hydroxymthylindol-4-yl)ethanol is stirred with 10 ml of absolute tetrahydrofuran and 0.6 ml of acetic anhydride for 18 hours at room temperature. The mixture is then concentrated, the residue taken up in ethyl acetate, washed with saturated sodium bicarbonate solution, and the organic phase is dried and concentrated. The residue is chromatographed over an aluminum oxide column (activity stage II; eluent: cyclohexane/ethyl acetate 1.5+1) and recrystallized from diisopropyl ether/hexane, thus obtaining 515 mg of acetic acid {7-benzyloxy-4-[2-(N-benzyl-N-tert-butylamino)-1-hydroxy-ethyl]indol-2-ylmethyl}ester, mp 133°–134° C.

C. 500 mg of the thus-obtained compound is hydrogenated in 20 ml of absolute tetrahydrofuran and 5 ml of acetic acid for 45 minutes in the presence of 40 mg of 10% palladium-carbon. The product is filtered, the filtrate concentrated, the residue triturated twice with absolute diethyl ether and twice with acetone/diethyl ether, thus obtaining 255 mg of acetic acid [4-(2-tert-butylamino-1-hydroxyethyl)-7-hydroxyindol-2-ylmethyl]ester acetate, decomposition point 162°–163° C.

EXAMPLE 35

229 mg of 2-(N-benzyl-N-tert-butylamino)-1-(7-benzyloxy-2-hydroxymethylindol-4-yl)ethanol is hydrogenated in 10 ml of methanol for 10 minutes in the presence of 40 mg of 10% palladium-carbon, filtered, the filtrate concentrated and recrystallized from ethanol/diisopropyl ether, yielding 95 mg of 2-(N-tert-butylamino)-1-(7-hydroxy-2-hydroxymethylindol-4-yl) ethanol, mp 150° C. (decomposition).

EXAMPLE 36

550 mg of acetic acid {-benzyloxy-4-[2-(N-benzyl-N-tert-butylamino-1-hydroxyethyl]indol-2-yl}methyl ester is hydrogenated in 20 ml of methanol for 30 minutes in the presence of 75 mg of 10% palladium-carbon. The reaction mixture is filteed, the filtrate is concentrated, and the residue is recrystallized from ethanol/diisopropyl ether, thus obtaining 285 mg of 2-(N-tert-butylamino)-1-(7-hydroxy-2-methylindol-4-yl)ethanol acetate, decomposition point 177°–178° C.

EXAMPLE 37

A. Under the conditions of Example 28 2.57 g of 4-chloroacetyl-7-hydroxyindole-2-carboxylic acid ethyl ester is reacted with 1.93 g of DL-3-aminobutyric acid benzyl ester and worked up, yielding 510 mg of 4-[N(2-benzyloxycarbonyl-1-methylethyl)aminoacetyl]-7-hydroxyindole-2-carboxylic acid ethyl ester, decomposition point 165°–169° C.

B. Under the conditions of Example 14(E), 300 mg of 4-[N-(2-benzyloxycarbonyl-1-methylethyl-)aminoacetyl]-7- hydroxyindole-2-carboxylic acid ethyl ester hydrochloride is hydrgenated and worked up, thus obtaining 110 mg of 4-[1-hydroxy-2-(2-carboxy-1-methylethylamino)ethyl]-7-hydroxyindole-2-carboxylic acid ethyl ester hydrochloride, decomposition point 176°–179° C.

EXAMPLE 38

A. Under the conditions of Example 14(D), 1.8 g of 7-hydroxyindole-2-carboxylic acid is reacted with 2.5 g of 3-(N-benzyl-N-cyanomethylamino)butyric acid methyl ester and worked up, thus producing 1.4 g of 4-[N-benzyl-N-(2-methoxycarbonyl-1-methylethyl-)aminoacetyl]-7-hydroxyindole-2-carboxylic acid hydrochloride, decomposition point 245°–250° C.

B. Under the conditions of Example 14(E), 1.1 g of 4-[N-benzyl-N-(2-methoxycarbonyl-1-methylethyl-)aminoacetyl]-7-hydroxyindole-2-carboxylic acid hydrochloride is hydrogenated and worked up, thus obtaining 420 mg of 4-[1-hydroxy-2-(2-methoxycarbonyl-1-methylethylamino)ethyl]-7-hydroxyindole-2-carboxylic acid hydrochloride which decomposes starting with 120° C.

EXAMPLE 39

A. Under ice cooling, hydrogen chloride is introduced for 8 hours into a solution of 19 g of 7-hydroxyindole-2-carboxylic acid ethyl ester and 5 g of s-triazine in 300 ml of tetrahydrofuran. The reaction mixture is then concentrated to dryness, combined with 200 ml of water and 200 ml of ethyl acetate, and agitated for 3 hours at room temperature. The organic phase is separated, the aqueous phase is extracted twice with ethyl acetate, the organic phases are combined and evaporated to dryness. The residue is extracted by boiling wth 200 ml of ethyl acetate, the resultant crystallized product is vacuum-filtered, and the yield is 5.8 g of 4-formyl-7-hydroxyindole-2-carboxylic acid ethyl ester, mp 210°–225° C.

B. 2.33 g of 4-formyl-7-hydroxyindole-2-carboxylic acid ethyl ester is combined with 1.8 ml of benzyl bromide, 1 g of potassium carbonate, and 100 ml of acetone and heated under reflux for 4 hours. The reaction mixture is then evaporated to dryness, combined with water, and extracted with ethyl acetate. The organic phase is washed twice with saturated sodium bicarbonate solution, dried over sodium sulfate, concentrated, and recrystallized from ethyl acetate/hexane, thus obtaining 1.8 g of 7-benzyloxy-4-formylindole-2-carboxylic acid ethyl ester, mp 131°–132° C.

C. 2.26 g of 7-benzyloxy-4-formylindole-2-carboxylic acid ethyl ester is heated in a mixture of 15 ml of 1N sodium hydroxide solution and 15 ml of ethanol for one hour to 100° C. The ethanol is then distilled off under vacuum, the mixture is acidified with 10% hydrochloric acid and the precipitate is vacuum-filtered. The product is recrystallized from glacial acetic acid, thus obtaining 2.22 g of 7-benzyloxy-4-formylindole-2-carboxylic acid, mp 207° C.

D. 500 mg of copper powder is heated in 30 ml of quinoline to 160° C. and 2 g of 7-benzyloxy-4-formylindole-2-carboxylic acid is added to the mixture. The mixture is heated to 220°–230° C. within 15 minutes and held at this temperature for 25 minutes. The reaction mixture is allowed to cool, poured into 150 ml of 10% hydrochloric acid, filtered, and the filtrate extracted three times with respectively 100 ml of ethyl acetate. The combined organic phases are dried, concentrated, and the residue chromatographed over a silica gel column with chloroform as the eluent. Yield: 780 mg of 7-benzyloxy-4-formylindole, mp 141°–142° C. (from methanol).

E. 500 mg of 7-benzyloxy-4-formylindole is combined with 50 mg of 4-dimethylaminopyridine, 0.7 ml of triethylamine, 0.5 ml of acetic anhydride, and 10 ml of dichloromethane and agitated for 24 hours at room temperature. The reaction mixture is then diluted with 50 ml of dichloromethane, washed with concentrated sodium bicarbonate solution; the organic phase is dried and concentrated. The residue is recrystallized from isopropanol, thus obtaining 400 mg of 1-acetyl-7-benzyloxy-4-formylindole, mp 77°–78° C.

F. A solution of 130 mg of 1-acetyl-7-benzyloxy4-formylindole in 5 ml of dimethylformamide is combined with 100 mg of trimethylsulfonium iodide and 45 mg of sodium hydride (80% in oil) and stirred for 20 hours at room temperature. The reaction mixture is then combined with 50 ml of water, extracted three times with ethyl acetate, the organic phase washed three times with saturated sodium chloride solution, dried, and concentrated.

The resultant oily product is dissolved in 5 ml of tert-butylamine and heated under reflux for 4 hours. The mixture is then evaporated to dryness, recrystallized from ethyl acetate/hexane, and the product is 90 mg of 7-benzyloxy-4-(1-hydroxy-2-tert-butylaminoethyl)indole, decomposing from 80° C.

G. Under the conditions of Example 14(E), 800 mg of 7-benzyloxyindole-4-(1-hydroxy-2-tert-butylaminoethyl)indole is hydrogenated and worked up, thus obtaining 40 mg of 4-(1-hydroxy-2-tert-butylaminoethyl)-7-hydroxyindoly, decomposing from 100° C. on.

EXAMPLE 40

A. One gram of 7-benzyloxy-4-(N-benzyl-N-tert-butylaminoacetyl)indole-2-carboxylic acid hydrochloride is combined with 650 mg of N-(2-hydroxyethyl)-morpholine, 366 mg of 4-dimethylaminopyridine, 450 mg of N,N'-dicyclohexylcarbodiimide, 5 ml of absolute dimethylformamide, and 15 ml of absolute tetrahydrofuran and agitated for one hour at 0° C. and for another 16 hours at room temperature. The reaction mixture is filtered, the filtrate is concentrated, the residue is taken up in ethyl acetate, washed four times with water; the organic phase is dried and concentrated. The residue is chromatographed over an aluminum oxide column (activity stage II; eluent: ethyl acetate/cyclohexane 2+1), yielding 440 mg of 7-benzyloxy-4-(N-benzyl-N-butylaminoacetyl)indole-2-carboxylic acid 2-(morpholino)-ethyl ester, mp 149°–150° C. (from ethyl acetate/diisopropyl ether).

B. 408 mg of 7-benzyloxy-4-(N-benzyl-N-tert-butylaminoacetyl)indole-2-carboxylic acid 2-(morpholino)ethyl ester is hydrogenated under the conditions of Example 14(E) and worked up, thus obtaining 250 mg of 7-hydroxy-4-(1-hydroxy-2-tert-butylaminoethyl)indole-2-carboxylic acid 2-(morpholino)ethyl ester monoacetate, decomposition point 177°–177.5° C. (from methanol/diethyl ether).

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

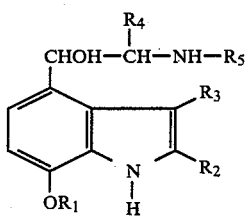

wherein $R_1$ is hydrogen or methyl;

$R_2$ is carboxy; phenoxycarbonyl; alkoxycarbonyl; cycloalkylalkoxycarbonyl; or alkylaminocarbonyl, each of up to 8 carbon atoms in total, and wherein the alkyl portion of each is optionally interrupted by an oxygen or nitrogen atom, or is substituted by carboxy;

$R_3$ is hydrogen or methyl;

$R_4$ is hydrogen or methyl; and $R_5$ is hydrogen; $C_{1-6}$-alkyl; $C_{2-6}$-alkenyl; or $C_{3-6}$-cycloalkyl;

or a physiologically acceptable salt thereof with an acid, or an alkali metal or alkaline earth metal salt thereof.

2. A compound of claim 1, wherein $R_1$ is hydrogen, $R_3$ is H or methyl and $R_4$ is H or methyl.

3. 4-(2-Amino-1-hydroxyethyl)-7-hydroxyindole-2-carboxylic acid methyl ester or the hydrochloride thereof, compounds of claim 1.

4. 4-(1-Hydroxy-2-methylaminoethyl)-7-hydroxyindole-2-carboxylic acid methyl ester or the hydrochloride thereof, compounds of claim 1.

5. 4-(1-Hydroxy-2-isopropylaminoethyl)-7-hydroxyindole-2-carboxylic acid methyl ester or the hydrochloride thereof, compounds of claim 1.

6. 4-(1-Hydroxy-2-isopropylaminoethyl)-7-hydroxyindole-2-carboxylic acid, a compound of claim 1.

7. 4-(2-tert-Butylamino-1-hydroxyethyl)-7-hydroxyindole-2-carboxylic acid methyl ester or the hydrochloride thereof, compounds of claim 1.

8. 4-(2-tert-Butylamino-1-hydroxyethyl)-7-hydroxyindole-2-carboxylic acid, a compound of claim 1.

9. 4-(2-tert-Butylamino-1-hydroxyethyl)-7-hydroxyindole-2-carboxylic acid ethyl ester or the hydrochloride thereof, compounds of claim 1.

10. 4-(2-tert-Butylamino-1-hydroxyethyl)-7-hydroxyindole-2-carboxylic acid n-butyl ester or the hydrochloride thereof, compounds of claim 1.

11. 4-(2-tert-Butylamino-1-hydroxyethyl)-7-hydroxyindole-2-carboxylic acid isobutyl ester or the hydrochloride thereof, compounds of claim 1.

12. 4-(2-tert-Butylamino-1-hydroxyethyl)-7-methoxyindole-2-carboxylic acid methyl ester or the hydrochloride thereof, compounds of claim 1.

13. 4-(2-tert-Butylamino-1-hydroxypropyl)-7-hydroxyindole-2-carboxylic acid ethyl ester or the hydrochloride thereof, compounds of claim 1.

14. 4-(2-Cyclohexylamino-1-hydroxyethyl)-7-hydroxyindole-2-carboxylic acid ethyl ester or the hydrochloride thereof, compounds of claim 1.

15. 4-(1-Cyclopropylamino-2-hydroxyethyl)-7-hydroxyindole-2-carboxylic acid ethyl ester, a compound of claim 1.

16. 4-(1-Hydroxy-2-tert-butylaminoethyl)-7-hydroxy-3-methylindole-2-carboxylic acid ethyl ester, a compound of claim 1.

17. 4-(1-Hydroxy-2-tert-butylaminoethyl)-7-hydroxy-3-methylindole-2-carboxylic acid, a compound of claim 1.

18. 4-(2-tert-Butylamino-1-hydroxyethyl)-7-hydroxyindole-2-carboxylic acid phenyl ester, a compound of claim 1.

19. 4-(2-tert-Butylamino-1-hydroxyethyl)-7-hydroxyindole-2carboxylic acid 2-dimethylaminoethyl ester, a compound of claim 1.

20. 4-(2-tert-Butylamino-1-hydroxyethyl)-7-hydroxyindole-2-carboxylic acid acetoxymethyl ester, a compound of claim 1.

21. 7-Hydroxy-4-(1-hydroxy-2-allylaminoethyl)indole 2-carboxylic acid ethyl ester, a compound of claim 1.

22. 7-Hydroxy-4-(1-hydroxy-2-tert-butylaminoethyl)indole-2-carboxylic acid trimethylacetoxymethyl ester, a compound of claim 1.

23. 7-Hydroxy-4-(1-hydroxy-2-tert-butylaminoethyl)indole-2-carboxylic acid methoxymethyl ester, a compound of claim 1.

24. 4-(1-Hydroxy-2-tert-butylaminoethyl)-7-hydroxyindole, a compound of claim 1.

25. A pharmaceutical composition comprising an amount of a compound of claim 1 effective to stimulate $\beta$-receptors in a patient and a pharmaceutically acceptable adjuvant.

26. A method of stimulating $\beta$-receptors in a patient in need of such treatment comprising administering to the patient an amount of a compound of claim 1 effective to stimulate $\beta$-receptors.

27. A method of claim 26, wherein the patient is suffering from bronchial asthma.

28. A method of preventing premature labor in a patient in need of such treatment comprising administering an effective amount of a compound of claim 1 to the patient.

29. A compound of claim 1 wherein $R_2$ is hydrogen, alkyl of up to 4 carbon atoms; hydroxyalkyl of up to 4 carbon atoms; hydroxyalkyl of up to 4 carbon atoms which is esterified by $C_{1-6}$ alkanoyl; carboxy; carboxy-$C_{1-4}$-alkyl; carboxy or carboxy-$C_{1-4}$-alkyl esterified by OR wherein R is $C_{1-8}$-alkyl, phenyl, $C_{1-4}$-alkoxy-$C_{1-4}$-alkyl, $C_{4-8}$-cycloalkylalkyl, $C_{1-4}$-alkanoyloxy-$C_{1-4}$-alkyl, or di-$C_{1-4}$-alkylamino-$C_{1-4}$-alkyl; or carboxy or carboxy-$C_{1-4}$-alkyl amidated by —$NH_2$, $C_{1-4}$-alkylamino- or —$NHCH_2COO$—$C_{1-4}$-alkyl.

30. A compound of claim 1 wherein $R_2$ is hydrogen, alkyl of up to 4 carbon atoms; hydroxyalkyl or up to 4 carbon atoms, hydroxyalkyl of up to 4 carbon atoms which is esterified by $C_{1-6}$ alkanoyl; carboxy; carboxy-$C_{1-4}$-alkyl; carboxy or carboxy-$C_{1-4}$-alkyl esterified by OR wherein R is $C_{1-8}$-alkyl, phenyl, $C_{1-4}$-alkoxy-$C_{1-4}$-alkyl, $C_{4-8}$-cycloalkylalkyl, $C_{1-4}$-alkanoyloxy-$C_{1-4}$-alkyl, or di-$C_{1-4}$-alkylamino-$C_{1-4}$-alkyl.

31. A compound of claim 1 wherein $R_1$ is $C_{1-6}$-alkyl or benzyl; $R_2$ is not H;

$R_3$ is $C_{1-16}$-alkyl; $R_4$ is $C_{1-6}$-alkyl; and $R_5$ is $C_{2-6}$-alkenyl, $C_{3-6}$-cycloalkyl, $C_{3-6}$-cycloalkylalkyl or one of $C_{1-6}$-alkyl, $C_{2-6}$-alkenyl, $C_{3-6}$-cycloalkyl or $C_{3-6}$-cycloalkylalkyl each substututed by COOH COOH esterified as defined for $R_2$, or phenyl substituted by OH, $C_{1-4}$-alkoxy, $C_{1-4}$-alkyl or halogen or $R_5$ is a $C_{1-8}$-polymethylene structure.

* * * * *